(12) United States Patent
Paolitto et al.

(10) Patent No.: US 8,317,696 B2
(45) Date of Patent: Nov. 27, 2012

(54) SURGICAL TOOL FOR MEASUREMENT OF VALVE ANNULUS AND CUSP GEOMETRY

(75) Inventors: Anthony Paolitto, St-Leonard (CA); Jonathan Paquette, Blainville (CA); Valerio Valentini, Montreal (CA)

(73) Assignee: Coroneo, Inc., Montreal, Quebec (CA)

( * ) Notice: Subject to any disclaimer, the term of this patent is extended or adjusted under 35 U.S.C. 154(b) by 179 days.

(21) Appl. No.: 12/654,183

(22) Filed: Dec. 14, 2009

(65) Prior Publication Data
US 2010/0217092 A1 Aug. 26, 2010

Related U.S. Application Data

(60) Provisional application No. 61/193,663, filed on Dec. 15, 2008.

(51) Int. Cl.
*A61B 1/32* (2006.01)
(52) U.S. Cl. .................. 600/235; 600/202; 600/208
(58) Field of Classification Search .................. 600/587, 600/201–246; 623/2.11; 33/511, 512
See application file for complete search history.

(56) References Cited

U.S. PATENT DOCUMENTS

| | | | |
|---|---|---|---|
| 4,211,241 A * | 7/1980 | Kaster et al. | 600/587 |
| 5,042,161 A * | 8/1991 | Hodge | 33/501.45 |
| 5,360,014 A * | 11/1994 | Sauter et al. | 600/587 |
| 5,489,296 A | 2/1996 | Love et al. | |
| 5,814,096 A * | 9/1998 | Lam et al. | 600/36 |
| 5,814,098 A | 9/1998 | Hinnenkamp et al. | |
| 6,322,526 B1 | 11/2001 | Rosenman et al. | |
| 6,350,281 B1 * | 2/2002 | Rhee | 623/2.11 |
| 6,371,968 B1 * | 4/2002 | Kogasaka et al. | 606/190 |
| 6,598,307 B2 * | 7/2003 | Love et al. | 33/512 |
| 6,846,324 B2 * | 1/2005 | Stobie | 623/2.11 |
| 7,258,698 B2 * | 8/2007 | Lemmon | 623/2.11 |
| 7,909,866 B2 * | 3/2011 | Stobie | 623/2.11 |
| 2008/0281232 A1 * | 11/2008 | Lansac et al. | 600/587 |
| 2010/0160832 A1 * | 6/2010 | Braido | 600/587 |

* cited by examiner

*Primary Examiner* — Ellen C Hammond
(74) *Attorney, Agent, or Firm* — Wood, Herron & Evans, L.L.P.

(57) ABSTRACT

A surgical tool for visually assessing or measuring the aortic structures contained within a generally tubular aortic root. The surgical tool is appropriately configured and sized to be insertable within an aortic root during surgery. The surgical tool comprises a handle portion and a cylindrical portion connectable thereto. The cylindrical portion defines an external cylindrical surface and extends in height along a tool axis between a base portion and a top portion. The cylindrical portion being optically clear or having at least a section thereof that is sufficiently transparent whereby, in use, when the surgical tool is placed within the aortic root and the aortic structures are in contact with the external cylindrical surface, the aortic structures are visible through said optically clear or sufficiently transparent section. The cylindrical portion preferably further comprises an array of reference datum and measurement increments visible through the optically clear section such that the visualization and measurement of the aortic structures may be effected with reference to the array.

15 Claims, 8 Drawing Sheets

SURGICAL TOOL FOR MEASUREMENT OF VALVE ANNULUS AND CUSP GEOMETRY

This application claims the benefits of U.S. Provisional Patent Application 61/193,663 filed Dec. 15, 2008.

FIELD OF THE INVENTION

The present invention relates to the field of cardiac surgery, and more specifically to the field of surgical instruments used in cardiac valve surgery or reconstructive surgery of the aorta.

BACKGROUND OF THE INVENTION

The mammalian heart is an organ made up of four muscular chambers that function together to pump blood throughout the body. Each of the four chambers has an associated downstream one-way valve made up of movable, coapting leaflets or cusps which cooperate to prevent the backward flow of blood, or regurgitation, into their respective chambers. Two such heart valves, the aortic and pulmonary valves, also commonly known as the semilunar valves, are characterized by three leaflets or cusps 91. The aortic valve leaflets 91 are attached within the aortic root 90, usually to a tri-scalloped or triple scalloped line of collagenous, fibrous tissue generally referred to as the valve annulus 92. As such, a three-pointed crown-like structure serves to support the aortic valve cusps or leaflets 91. The U-shaped convex lower edges of each leaflet are attached to, and suspended from, the base 97 of the aortic root 90, with the upper free edges or margins 93 of each leaflet being free to move and project into the lumen of the aorta 99. Two adjacent leaflets approach one another at one of the three points of said crown-like structure to define a commissure 95 of the aortic valve. Behind each leaflet 91, the aortic vessel wall bulges outward, forming a pouch-like dilatation known as the sinus of Valsalva 98. In the region located slightly above the level of the commissures 95, the aortic root 90 creating the sinuses of Valsalva 98 merges into the substantially tubular portion of the ascending aorta 99 at a substantially planar transition zone commonly known as the sinotubular junction (STJ) 100. The aortic root 90 houses the aortic valve structures and generally includes the portion of the native aortic conduit extending form the left ventricular outflow tract (LVOT) to the portion of ascending aorta 99 slightly above the sinotubular junction (STJ). Typically, aortic root reconstructions or interventions usually involve the aortic valve, while ascending aorta interventions usually exclude the aortic valve and involve the native aortic conduit located generally downstream of the sinotubular junction. In some patients, one or two of the native valve cusps may be congenitally fused and a bicuspid or, more rarely, a unicuspid aortic valve may present.

Figure 5:
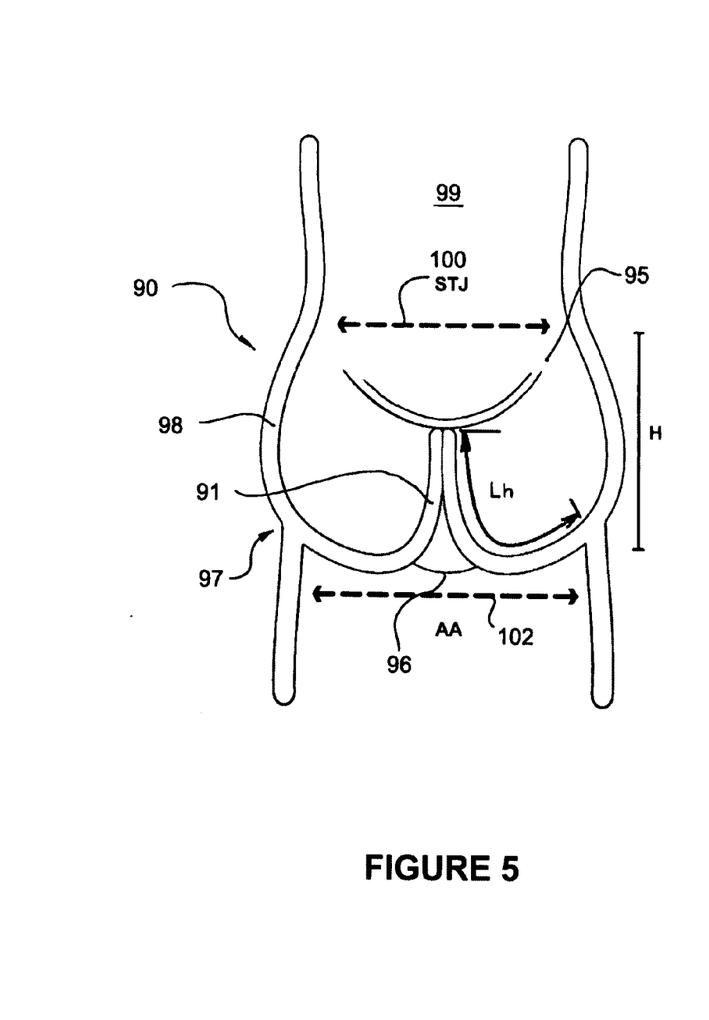
FIG. 5 is a schematic cross-sectional side view of aortic root 90 including the native valve cusps 91, prior to deployment of the surgical tool 10 in FIG. 1.
Figure 6:
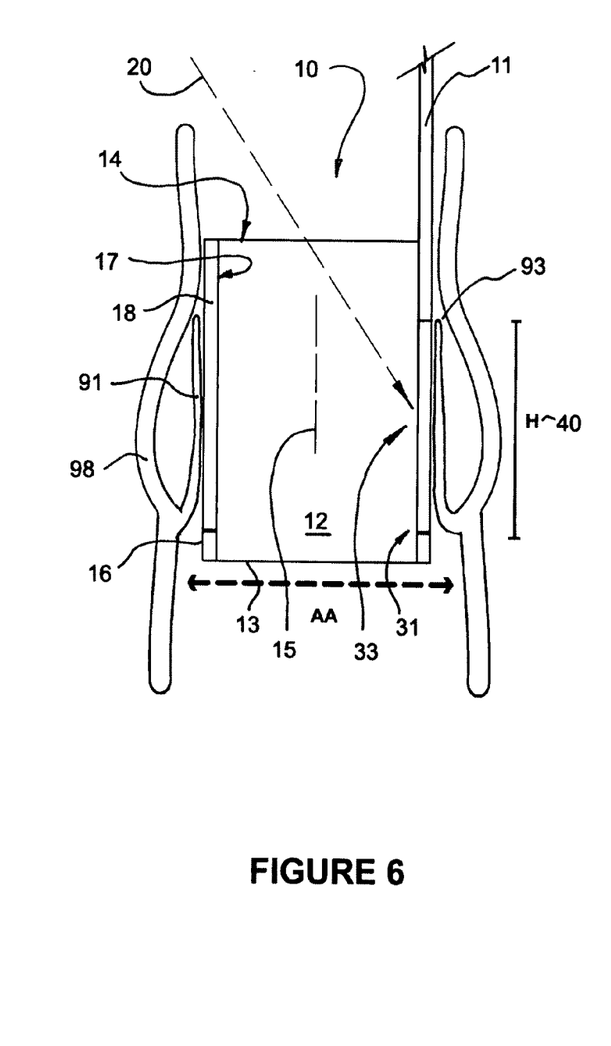
FIG. 6 is a schematic cross-sectional side view of the aortic root 90 illustrated in FIG. 5, illustrating the surgical tool 10 of FIG. 1A in a deployed state.

Aortic root dilation is one of the most common causes of aortic valve incompetence in North America. Prevalence of surgical corrections for this pathology has increased considerably during the last two decades. There are a variety of surgical corrections (for example the Reimplantation technique popularized by David, or the Remodelling technique popularized by Yacoub) that have been developed over the years to surgically repair an aortic valve or reconstruct the aortic root portion of the ascending aorta. In most surgeries, especially conservative aortic valve surgery which restores valve competence in regurgitant aortic valves having occurred from a dilatation of the aortic root or a retraction of valve cusps, surgeons must assess the amount of dilatation in the aortic root and the size of native cusps in order to inform the reconstruction of said structures. Currently, calibrated cylindrical sizers such as Hegar dilators, or calibrated prosthetic valve sizers used to measure native valve annulus prior to implanting a prosthetic valve, are used. Such instruments are limited in their use in that they can only measure the internal diameter of the aortic root (schematically illustrated in FIG. 5, and labelled AA at the base of the aortic root and STJ at the level of the sinotubular junction). To measure, for instance, the geometric height of the valve cusp 91 (i.e. the distance between nadir 96 and nodulus of arantius 94) a ruler or scale that is usually not sized or configured appropriately for measurement of valve cusps, must be used in a second separate set-up, once the Hegar dilator is removed from within the aortic root to visually expose the valve cusp. Measurement of the distance between commissures 95 is also challenging since the aortic root 90 is not pressurized and does not retain its substantially tubular geometry especially when aneurysmal sinuses of Valsalva 98 have been resected leaving behind a scalloped aortic root.

There is room for improvement in providing a surgical tool or instrument that can measure the internal diameter of the aortic annulus 92 at the virtual basal ring 102 location, or the aortic root diameter AA, and simultaneously also visually assess and measure the geometry of the valve cusps while said tool or instrument remains inserted within the aortic root. As such, the spatial relationship of the native aortic structures may be assessed and measured. Such measurements obtained by said surgical tool are useful in informing the surgeon of the extent of surgical reconstruction required to be performed on the aortic root or aortic valve contained therein.

Accordingly, there exists a need for a measuring tool or implement for use in valve surgery that can provide the following benefits: i) measurement of at least one of the internal diameters of the aortic root, aortic annulus, basal ring diameter or sinotubular junction, ii) geometric height of the valve cusp (dimension between the nadir and nodulus of arantius), iii) height of the commissure (dimension from the basal diameter of the aortic root to the commissure peak), iv) angle between two commissures, and v) circumferential length between two commissures.

It is also a further advantage if the surgical tool can also have additional functions to size or tailor a prosthetic aortic conduit in conservative aortic valve surgeries where the native valve cusps are preserved, but there exists the need to replace aneurysmal aortic root tissue, such as the Sinuses of Valsalva, or an aneurysmal ascending aorta with a tailored prosthetic conduit.

SUMMARY OF THE INVENTION

It is a general object of the present invention to provide such an improved surgical tool and associated surgical method for use in aortic valve-sparing procedures, or other aortic valve or aortic root reconstruction surgeries.

Advantages of the present invention include that the proposed surgical tool, allows the surgeon with the insertion of one surgical tool in the aortic root, to quickly assess the aortic structures or anatomic parameters of the native aortic root complex including cusp structures. As such, these parameters can advantageously inform the surgeon of the extent of reconstruction required and suitable size of aortic implant that may be required to perform an effective reconstruction or replacement surgery.

BRIEF DESCRIPTION OF THE DRAWINGS

Various embodiments of the present invention will now be disclosed, by way of example, in reference to the following drawings in which.

DETAILED DESCRIPTION

Referring to FIGS. 3-6, the anatomic features or aortic structures of the aortic root complex 90 will now be described in greater detail with reference to a three cusp or tricuspid aortic valve 89. Each of the valve leaflets or cusps 91 are attached at the scalloped insertion line 88 which follows the scalloped fibrous tissue referred to as the aortic valve annulus 92. The generally half-circle cusps 91 extend from said insertion line to their unattached free margin 93. The lowest insertion point of the cusp is known as the nadir 96. The diameter or plane through the three nadirs is known as the basal ring or basal diameter 102. The approximate midpoint of the free margin is characterized by a local cusp thickening known as the nodulus of Arantius 93. Free margins 93 of adjacent cusps 91 meet at the aortic wall to define commissures 95. The pouch-like bulbous portions of aortic root wall behind cusps 91 define the sinuses of Valsalva 98. The substantially triangular zone of aortic wall located below the cusp insertion line 88 of adjacent cusps and above the basal ring diameter 102 is the interleaflet triangle 103 (shown delimited by dashed lines in FIG. 3). Two of the three sinuses of Valsalva include coronary ostia 104.

The anatomic features or aortic structures of the aortic root serve as landmarks or anatomic datum to guide the surgeon during aortic valve surgery or reconstructive surgery of the aortic root complex.

Figure 1A:
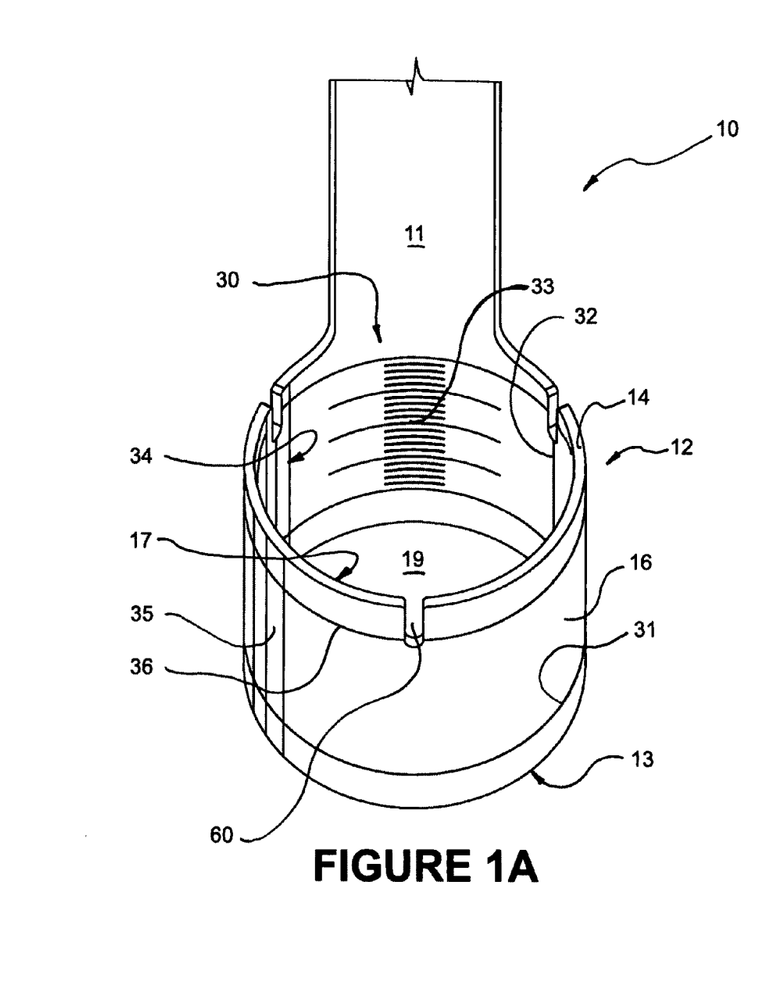
FIG. 1A in a perspective view illustrates a surgical measuring tool 10 in accordance with a first preferred embodiment of the present invention for use in aortic valve surgery or aortic root reconstruction surgery.

Referring to FIG. 1A, there is shown a surgical measuring tool, instrument or implement 10 in accordance with a first embodiment of the present invention. Tool 10 is described here below and shown throughout the figures in the context of use during a repair an aortic valve 89 or reconstruction surgery of the aortic root 90. It should however be understood that tool 10 may be used in other surgical contexts where a cardiac valve is contained in a tubular conduit, without departing from the scope of the present invention. For example, surgical tool 10 may be used in the context of surgical repair of a pulmonary cardiac valve.

In a first embodiment, surgical measuring tool 10 is comprised of a handle portion 11 and a substantially cylindrical or tubular functional end or portion 12 configured and sized for insertion within an aortic root 90 of a patient's aorta 99. Functional end 12 is provided in a variety of calibrated external diametrical sizes to be able to measure the internal diameter of aortic root 90, and more specifically internal diameter of basal diameter 102 of aortic annulus 92, or internal diameter of aortic root 90 at the level of sinotubular junction 100. Functional end 12 extends in height from a base plane or portion, or lower section 13 to a top plane or top portion, or upper section 14 along a device longitudinal axis 15. Tubular end 12 is defined by an external cylindrical surface 16 and an internal cylindrical surface 17 inwardly offset therefrom by a radial thickness 18. Internal cylindrical surface 17 defines a cylindrical cavity or channel 19. Handle 11 extends from tubular end 12 in a direction generally aligned with device axis 15.

Surgical tool 10 is preferably manufactured as a unitary, one part construction wherein both the handle portion 11 and tubular portion 12 are fabricated from the same material and fabrication process. For instance, surgical tool 10 may be fabricated from a plastic injection process. The material of surgical tool 10 is a surgical grade plastic material which may be produced with sufficient transparency or translucency to allow a surgeon to see or visualize aortic structures or features of the aortic root across an optically clear section, such as wall thickness 18 when said surgical tool 10 is deployed, during use, within the aortic root 90 of a patient. The material properties of functional end 12 must be such that when tubular end 12 is produced with a predetermined wall thickness 18, the resultant tubular wall is either clear, see-through, or of sufficient translucency to allow surgeon to visualize the aortic structures of the aortic root when said features are in proximity or in contact with external cylindrical surface 16.

Alternatively, surgical tool 10 may be produced from a glass material, preferably having break resistant properties, and which may also be resterilized and reused. Alternatively still, the handle portion 11 may be produced from a metallic material and the tubular end 12 from a plastic or glass material, and handle may be permanently or demountably connected to tubular end 12. In all embodiments, at least a portion of tubular portion 12 must have a substantially transparent or sufficiently translucent wall thickness to allow surgeon to see across said transparent or translucent wall thickness, and observe or be able to visually assess anatomic aortic structures that are in contact with external cylindrical surface 16 when tool 10 is inserted in aortic root 90.

Alternatively still, tubular end 12 may be produced from a material which is configured to magnify the anatomic features in proximity or contact with external surface 16 and which are visible through said optically clear section or tubular wall 18, when said surgical tool 10 is placed within aortic root 90 and surgeon views internal surface 17 along a line of sight 20 having access thereto.

Tool 10 is preferably made in a variety of calibrated diametrical sizes such that external surface 16 may be used to measure or gage the internal diameter of the aortic root 90. For example, the variety of sizes may be 23, 25, 27, 29, 31, 33 mm diameter (or 22, 24, 26, 28, 30, 32, 34 mm diameter) to cover the range of anatomic sizes of aortic roots. As such, tool 10 may be used to measure the diameter of basal ring 102 corresponding to aortic annulus 92, sinotubular junction diameter 100, or a diameter of ascending aorta 99. The height of tubular end 12 (distance between base 13 and top 14 portion) is preferably at least the magnitude of the diameter of external surface 16.

Figure 1B:
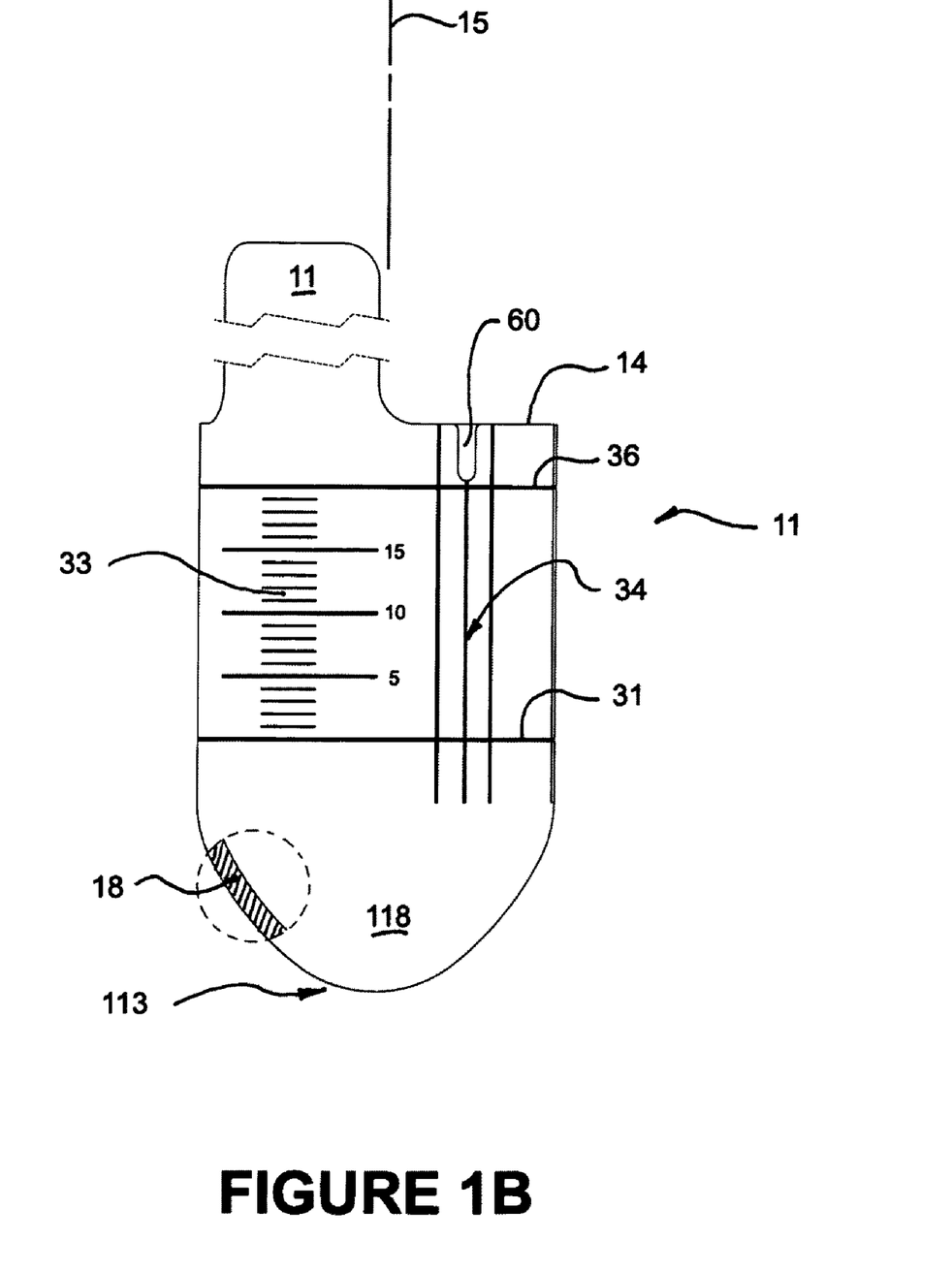
FIG. 1B in a side elevation view illustrates a variant 11 of the measuring tool in FIG. 1A having a progressively narrower terminal end 118 in order to facilitate insertion of said measuring tool within the aortic root 90.

The preferred embodiment of tool 10 is illustrated with an open tubular end 12, such that base portion 13 and top portion 14 are in open communication. As such, the surgeon or user has a line of sight 20 to internal surface 17 when tool 10 is placed within the aortic root. Alternatively, the base portion 13 of tool 10 may be partially closed by a substantially annular partition or entirely closed by a flat disc or bowl-shaped partition or wall. As well, the base portion 13 of tool 10, which represents the tool leading edge that is first inserted within aortic root 90, may be configured with a progressively smaller diameter or profile so as to facilitate insertion of said tool within aortic root 90. For example, such profile may be a spherical, bullet-shaped, parabolic, or chamfered or beveled surface, extending below base portion or plane 13. Referring to FIG. 1B, a variant 11 of tool 10 is illustrated with a closed bottom portion 113, said portion being configured with a substantially bullet shaped profile. Wall thickness 18 is maintained within bullet-shaped bottom portion 113. In all of the above variants, although bottom portion of surgical tool may be partially or fully closed, the surgeon or user still has line of sight to internal surface 17 through open top portion 14.

In other variants of the surgical tool 10, top portion 14 may also be fully or partially closed by an optically clear or translucent material to form a top partition or wall or surface. This top surface may be sufficiently translucent or optically clear to allow surgeon to visualize internal surface 17, either in a 1:1 optical representation, or may be produced with magnification optical properties to magnify or enhance the visualization of internal surface 17, and more specifically the aortic structures or anatomic markers of the aortic root when the latter are in contact with external surface 16. Alternatively still, the tubular portion 12 may be replaced by an optically clear cylindrical portion having a top portion and external cylindrical surface. The internal construction of cylindrical portion is such that refractive and reflective properties of light are exploited that when an anatomic feature of the aortic root is in contact with external surface 16, the anatomic feature is visible on or through top portion 14 either in true 1:1 optical representation, or preferably magnified representation. It is also conceivable to have reduced magnification representation. Embodiments illustrating the above principles and concepts will be described in greater detail below with reference to FIGS. 7A-9B.

Figure 2:
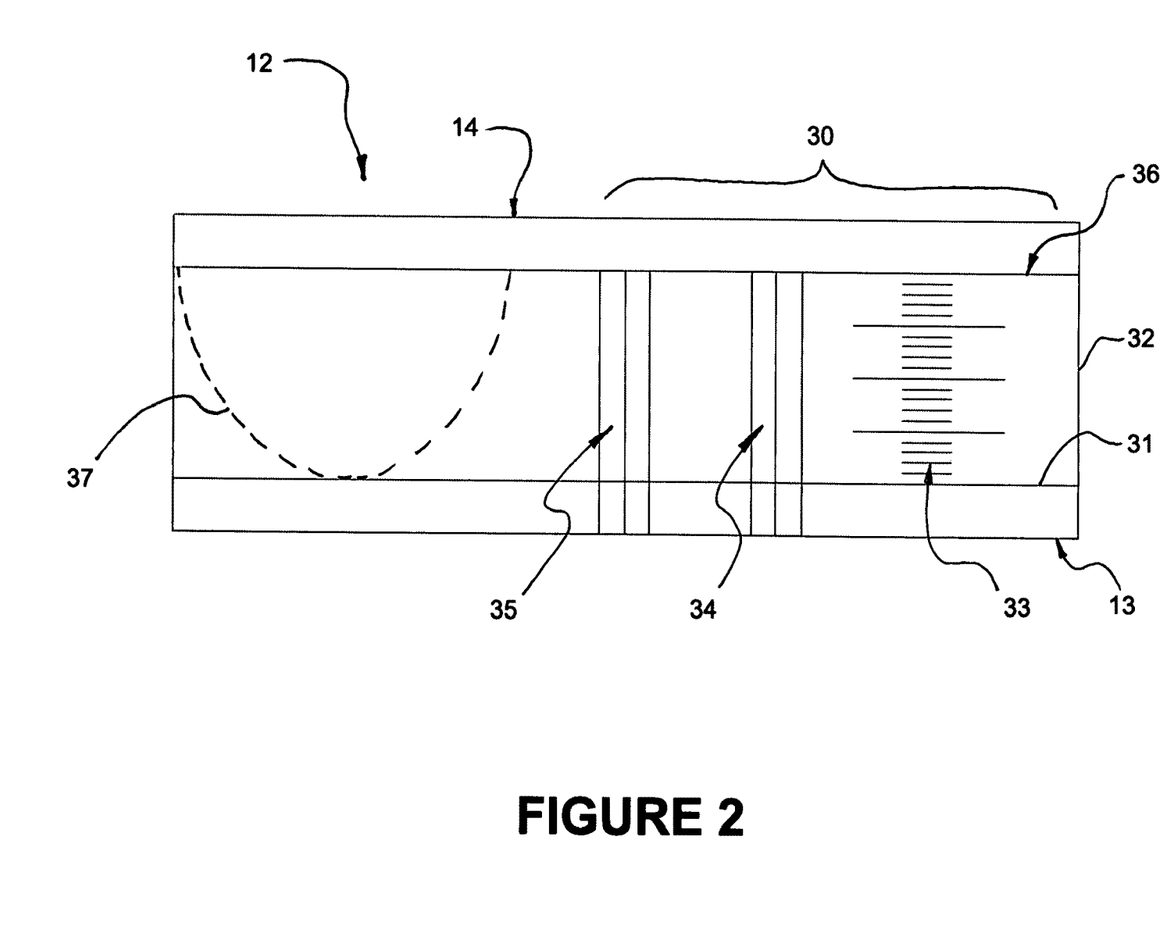
FIG. 2 in a flat wrap view illustrates an array 30 of reference datum and measurement increments of the surgical measuring tool 10 illustrated in FIG. 1A.
Figure 3:
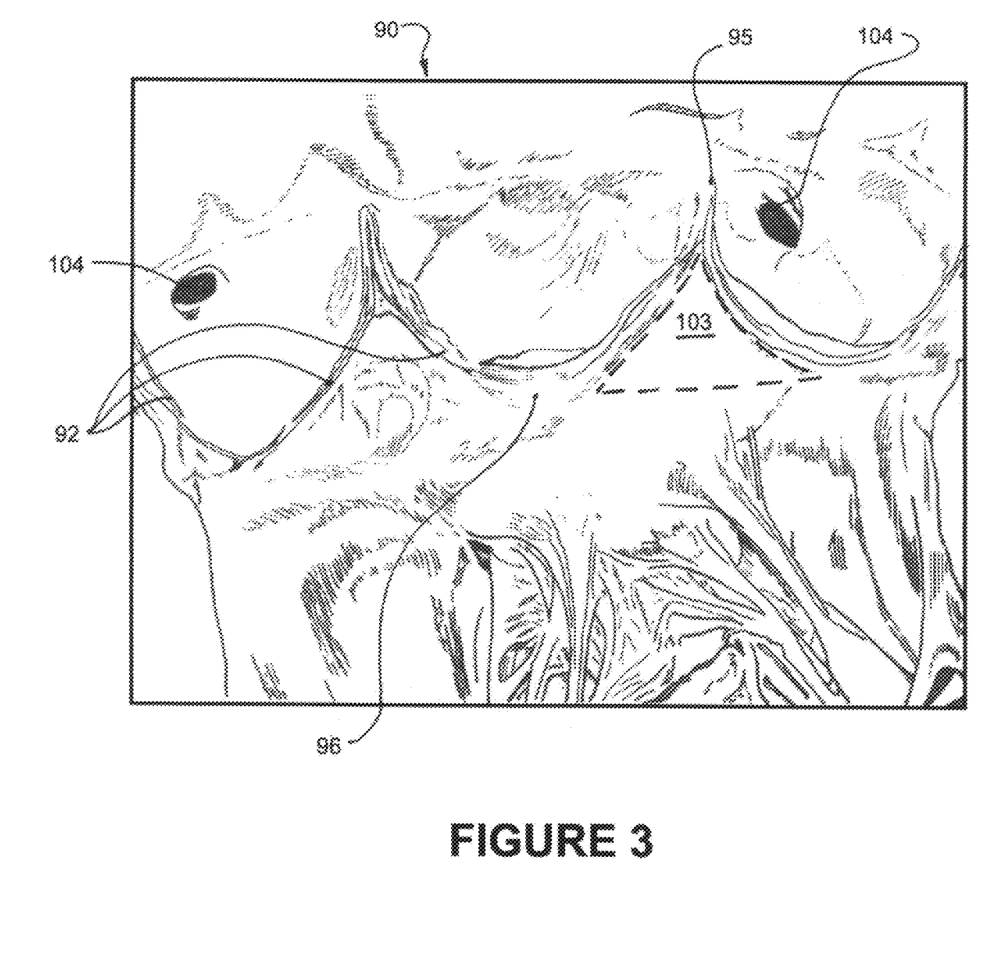
FIG. 3 is a picture of a native aortic root 90 that has been flat-wrapped to show the aortic structures of same, except for the valve cusps which have been resected.
Figure 4:
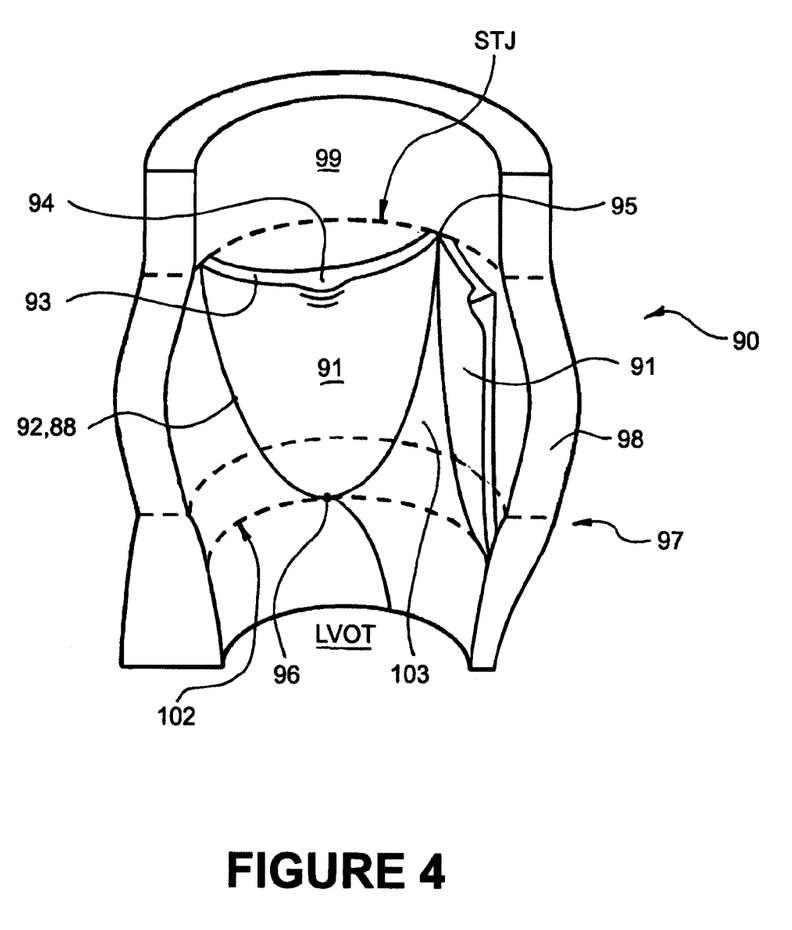
FIG. 4 is a schematic cut away view of the aortic root 90 into which will be deployed the surgical measuring tool 10 of FIG. 1A or 11 of FIG. 1B, according to the present invention.

Referring to FIGS. 1A, 1B, and 2, surgical tool 10, 11 is provided with an array 30 of reference datum and spaced apart measurement increments, which will now be described in greater detail. Although FIG. 2 illustrates an exemplary array, other different arrays are also possible without departing from the principles of the present invention. The functional requirement of such an array and the layout of reference datum and measurement increments serves to provide the surgeon with the ability to visually observe and measure the spatial relationship between aortic structures of the aortic root, or to measure the dimension of a given aortic structure. For example, the surgeon can measure the geometric height 40 of a valve cusp 91, or the height of a commissure 95 above the basal ring diameter 102, or the angular spacing or distance between adjacent commissures 95.

With reference to FIG. 2, array 30 is preferably provided with a first horizontal reference datum 31 in the nature of a baseline diameter. Said baseline diameter is located proximally to the base portion 13 and defines a baseline plane perpendicular to device axis 15. In use, said first reference datum may be aligned with the nadir 96 of one or several cusps 91. Diametrical indicator 36 serves as an additional horizontal reference which may guide the surgeon in ensuring all of one or several anatomic features must lie for instance between first datum 31 and indicator 36.

Array 30 is also preferably provided with a second vertical reference datum 32 extending along the height of functional end 12, said second datum being perpendicular to said first datum. In use, second reference datum 32 may be aligned with a commissure 95. Vertically offset above first datum 31 is a scale member consisting of a plurality of height measurement increments 33 which may be used to measure the height of an aortic structure or anatomic feature relative to baseline diameter 31, or relative to another anatomic feature that is aligned with the baseline diameter 31. For instance, the height of commissure 95 relative to the basal ring 102 may be measured by said height measurement increments 33. The height increments may be of varying circumferential length to distinguish between major and minor height subdivisions. The measurement increments may also be identified by a numeral, letter or other distinctive marker or reference to facilitate measurement or assessment of aortic structures. For example, surgical tool 11 is provided with numerals "5", "10", "15" adjacent height measurement increments 33. Alternatively still, the increments may be of a certain color or texture to improve visualization.

A plurality of vertically extending increments 34, circumferentially offset relative to vertical reference datum 32 are provided. Increments 34 are disposed at 120 degrees in angular relationship to vertical datum 32. Increments 34 are spaced by a predetermined distance to represent a change in angle dimension or change in circumferential length as a function of the diametrical size of the surgical tool cylindrical portion 12. For example, increments 34 may be spaced 5 degrees apart or more increments may be added for finer resolution in measuring with spacing of 2 degrees apart. Such an angular relationship is advantageous in measuring commissure spacing or cusp geometry in the case of tricuspid aortic valves where three cusps are located approximately 120 degrees apart. In the case that a bicuspid aortic valve presents, a second plurality of vertical increments 35 is provided and disposed at 180 degrees in angular relationship to vertical datum 32.

To account for parallax effect in measuring the size of anatomic structures, or measuring the spatial relationship between anatomic structures, when array 30 is viewed along a viewing axis such as line of sight 20, the spacing of measurement increments 33 may be selectively adjusted to compensate for measurement error resulting from said parallax effect. For instance, a given spacing of measurement increments 33 that reads 1 mm spacing is actually spaced more or less than 1 mm to account for said parallax effect and compensate measurement error.

Alternatively, functional end 12 may be provided with one or several curved indicators 37 that may be used to measure the length of a cusp insertion line in a given cusp when said curved indicator is aligned with the cusp insertion line.

To enhance its functionality during aortic valve sparing surgery which requires the use of a prosthetic vascular conduit to replace aneurismal aortic tissue, top portion 14 may be configured with a plurality of angularly spaced demarcation features 60. As illustrated, demarcations 60 are illustrated as axially extending slots or slits. Other features are also possible such as grooves in external cylindrical surface 16, or visual demarcations or indicators or ridges on the internal surface 17. Said demarcations are spaced a predetermined amount, for example 120 degrees or 180 degrees or other predetermined advantageous spacing, to allow marking of a tubular vascular prosthesis at said demarcation features when said prosthesis is placed over said cylindrical portion 12 of surgical tool 10.

One example of a surgical method for use of surgical tool 10 comprises the following steps:

Select a calibrated size of surgical tool 10;
Insert tool 10 into aortic root 90 to measure an internal diameter of said aortic root;
Repeat until correct size of surgical tool is determined to adequately measure the desired internal aortic root diameter;
Align lower datum 31 with the nadir 96 of a valve cusp 91;
Measure the geometric height of said valve cusp by reading height increment 33 which aligns closest to nodulus of arantius 94 of said cusp 91;
Rotate surgical tool 10 within aortic root, if necessary, and measure the height of commissures 95 above the basal ring 102 by reading height increment 33 which aligns closest to target commissure being measured;
Align vertical reference datum 32 with a commissure 95 and measure the angular relationship (or distance) between adjacent commissures by reading vertical spanning increments 34 (if tricuspid valve) or increments 35 (if bicuspid valve).

Figure 7A:
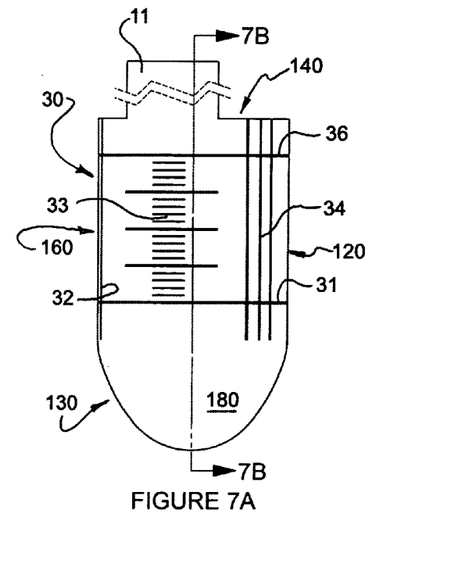
FIG. 7A in a side elevation view illustrates a surgical measuring tool 100 in accordance with a second embodiment of the present invention for use in aortic valve surgery or aortic root reconstruction surgery.
Figure 7B:
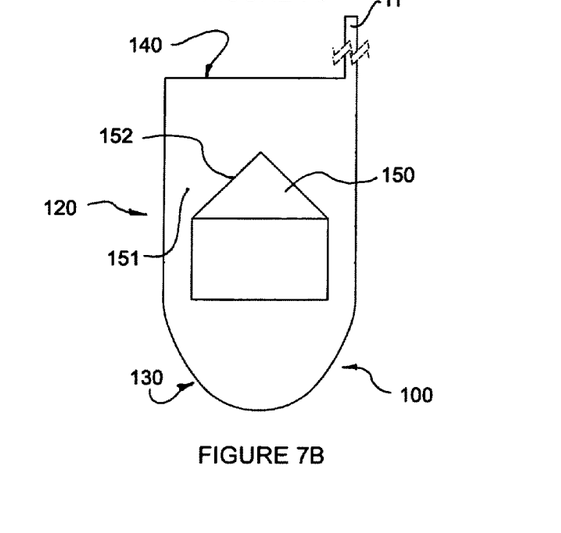
FIG. 7B in a cross-sectional side view along section line 7B-7B of the measuring tool 100 of FIG. 7A, illustrates a conical mirror 150 for reflecting array 30 on top portion 140 of surgical tool 100.
Figure 7C:
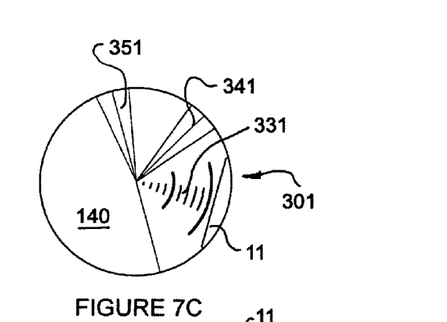
FIG. 7C in a top view of measuring tool 100 of FIG. 7A illustrates a reflected measurement array 301 reflected on top portion 140 of surgical tool 100 by a conical mirror 150.

Referring now to FIGS. 7A-7C, a second embodiment of the present invention will now be described in greater detail. Surgical tool 100 is comprised of a handle portion 11 and a substantially cylindrical portion 120. Handle portion 11 is either permanently mounted to top portion 140 of cylindrical portion 120, or demountable connected thereto so that a solitary handle may interchangeably be coupled to a variety of different incrementally sized cylindrical portions 120 so as to enable calibrated measurement of the internal diameter of the aortic root 90. Bottom portion 130 is configured with a progressively smaller diameter or profile to ease insertion into said aortic root. As illustrated, bottom portion 130 is configured with a substantially bullet shaped or parabolic profile 180. Other, progressively smaller profiles are also possible to ease insertion of measuring tool 100 into an aortic root, such as, for instance, a substantially conical or generally spherical or truncated conical profile. Top portion 140 is generally circular and planar.

Similar to the first embodiment 10, second embodiment 100 includes an array 30 of reference datum 32, 31, 36 and measurement increments 33, 34, 35 in an optically clear or sufficiently transparent section of cylindrical portion 120. Within cylindrical portion 120 is included an angled mirror arrangement such as preferably conical mirror 150 for optically reflecting aortic structures to be visible on top portion 140 when said structures are in proximity or contact to external surface 160 of cylindrical portion 120. Volume 151 between array 30 (which is disposed generally adjacent to external cylindrical surface 160) and optically reflective surface 152 of conical mirror 150 is void, optically clear or sufficiently transparent or translucent to allow passage of light. As such, aortic structures and measurement increments 33, 34, 35 of array 30 may be advantageously reflected on said mirror surface 152 and projected on top portion 140 where they may be visibly seen by surgeon. Array 30 is visible on top portion 140 as reflected measurement array 301, measurement increments 33, 34, 35 as reflected increments 331, 341, 351, respectively, and datum 32 as reflected datum 321. In this embodiment, measurement increments 33 and reflected increments 331 are in substantially 1:1 spacing relationship.

Figure 8A:
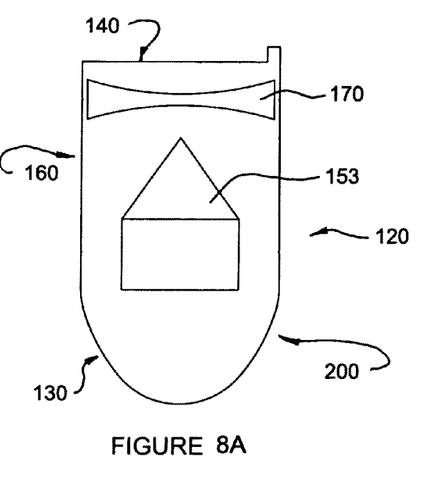
FIG. 8A in a cross-sectional side view illustrates a surgical measuring tool 200 in accordance with a third embodiment of the present invention for use in aortic valve surgery or aortic root reconstruction surgery, said tool 200 including an optical lens member 170 for refracting light being reflected by a conical mirror 153.
Figure 8B:
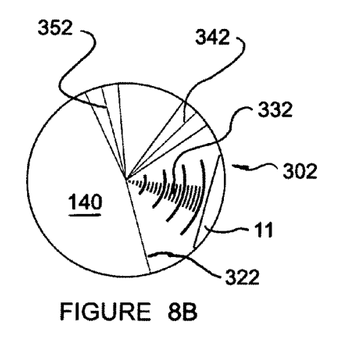
FIG. 8B in a top view of the measuring tool 200 of FIG. 8A illustrates a reflected measurement array 302 reflected by conical mirror 153, said reflected measurement array having been reduced in magnification by optical lens member 170 relative to array 30.

Referring to FIGS. 8A-8B, a third embodiment of the present invention will now be described in greater detail. Surgical tool 200 is similar to tool 100 except that it further comprises at least one optical lens member 170 for refracting the light reflected by conical mirror 153 a predetermined amount. In this embodiment, optical lens 170 is of a generally concave geometry. Tool 200 requires at least one lens member, but depending on the amount of refraction desired or optical manipulation sought, a pair, or even a plurality of cooperating lens members may be advantageously used.

With reference to FIG. 8B, optical lens 170 refracts light by a predetermined amount in a manner that reduces the magnification of the aortic structures being reflected by conical mirror 153, refracted by lens 170 and visible on top portion 140. As such, measurement increments 332 in reflected measurement array 302 are closer together than the measurement increments 33 in the array 30. As well, the aortic structures in contact with said external cylindrical surface 160 visibly appear on said top portion 140 smaller than they actually are at the contact location with said surgical tool.

Figure 9A:
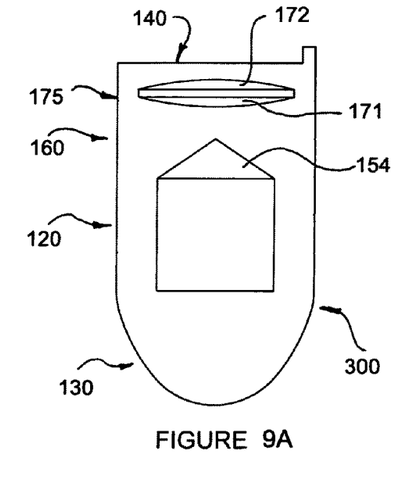
FIG. 9A in a cross-sectional side view illustrates a surgical measuring tool 300 in accordance with a fourth embodiment of the present invention for use in aortic valve surgery or aortic root reconstruction surgery, said tool 300 including an optical lens arrangement 175 for refracting light being reflected by a conical mirror 154.
Figure 9B:
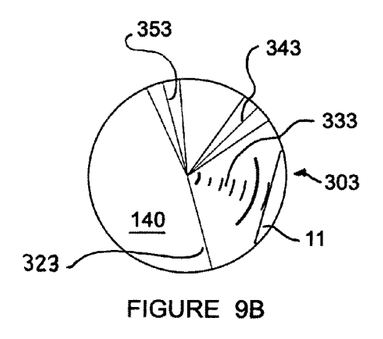
FIG. 9B in a top view of the measuring tool 300 of FIG. 9A illustrates a reflected measurement array 303 reflected by conical mirror 150 and having been increased in magnification by optical lens arrangement 175.

FIGS. 9A-9B illustrate a fourth embodiment of the present invention whereby surgical tool 300 includes an optical lens arrangement 175 for refracting light being reflected by a conical mirror 154 onto top surface 140. Lens arrangement 175 is comprised of a pair of substantially convex lenses 171, 172 cooperating to refract light by a predetermined amount in a manner that increases the magnification of the aortic structures being reflected by conical mirror 154, refracted by lenses 171, 172 and visible on top portion 140. As such, measurement increments 333 in said reflected measurement array 303 are spaced further apart than the measurement increments 33 in the array 30. As well, the aortic structures in contact with said external cylindrical surface 160 visibly appear on said top portion 140 larger than they actually are at the contact location with said surgical tool.

The invention claimed is:

1. A surgical tool for visually assessing the aortic structures contained within a generally tubular aortic root of a patient, the aortic root including an aortic valve, the aortic valve defining a valve axis, the aortic root extending in height along the valve axis between a root base portion located in proximity to a left ventricular outflow tract and a spaced away root sinotubular portion located in proximity to a sinotubular junction, the aortic valve attached to the aortic root through a scalloped valve annulus extending circumferentially around the valve axis, the aortic valve including a plurality of valve cusps connected to the valve annulus, the valve cusps each having a free margin portion spaced from the valve annulus, the free margin including a nodulus of arantius at a substantially midspan location, the valve cusps each defining a nadir at the attachment point with the valve annulus closest to the root base portion, the valve cusps having a geometric height defined by the distance between the nadir and nodulus of arantius, the valve cusps collectively defining commissures at the junction of each of two adjacent cusps in proximity to the valve annulus, said surgical tool comprising:

a substantially cylindrical portion, said cylindrical portion defining an external substantially cylindrical surface, said cylindrical portion extending in height along a tool axis between a base portion and a top portion, said cylindrical portion appropriately configured and sized for insertion within the aortic root, said cylindrical portion having a sufficiently optically clear section, whereby, in use, when said surgical tool is placed within the aortic root and the aortic structures are in contact with said external cylindrical surface, the aortic structures are visible through said optically clear section;

wherein said cylindrical portion further comprises an array of reference datum and measurement increments visible through said optically clear section, and whereby, in use, visualization and measurement of the aortic structures may be effected with reference to said array; and     wherein said surgical tool further comprises a generally elongate handle portion, said handle portion connected to said cylindrical portion for manipulating said surgical tool during insertion of said tool in the aortic root.

2. The surgical tool of claim 1, wherein said cylindrical portion is substantially hollow and defines a cavity therewithin, said cavity delimited in part by an internal substantially cylindrical surface, said internal cylindrical surface being offset inwardly from said external cylindrical surface to define an annular wall between said external and internal surfaces, said optically clear section contained within at least a portion of said annular wall, the aortic structures being visible when line of sight accesses said internal cylindrical surface.

3. The surgical tool of claim 2, wherein said base portion is configured with a progressively narrower terminal end relative to said external cylindrical surface in order to facilitate insertion of said tool within the aortic root.

4. The surgical tool of claim 2, wherein said internal cylindrical surface extends between said top and base portions, and said hollow cavity is a through passage communicating with said top and base portions.

5. The surgical tool of claim 1, wherein when said surgical tool is placed within the aortic root, the internal diameter of the aortic root may be measured by the calibrated diametrical size of said external cylindrical surface, and while said surgical tool is kept in place, said visualization and measurement of the aortic structures may be effected.

6. The surgical tool of claim 5, wherein said array includes a baseline diameter perpendicular to said tool axis and located in proximity to said base portion, and also includes a plurality of spaced apart height increments disposed axially away from said baseline diameter along said tool axis, whereby, in use, when said baseline diameter is aligned with the nadir of a valve cusp, said array allows said measurement of the cusp geometric height with reference to said height increments.

7. The surgical tool of claim 6, wherein said height increments allow the measurement of the height of the commissures when said baseline diameter is aligned with the nadirs of the valve cusps.

8. The surgical tool of claim 7, wherein said array further includes a plurality of spaced apart vertical increments parallel to said tool axis and orthogonal to said height increments, and whereby, in use, when said baseline diameter is aligned with the nadir of a valve cusp, said vertical increments allow measurement of angular relationship between adjacent commissures.

9. The surgical tool of claim 8, wherein said vertical increments allow the measurement of the distance between commissures when said vertical increments are aligned with said commissures.

10. The surgical tool of claim 1, wherein said surgical tool includes a conical mirror within said cylindrical portion, said mirror allows the aortic structures to be reflected and visible on said top portion when the aortic structures are in contact with said external cylindrical surface and visible through said optically clear section.

11. The surgical tool of claim 10, wherein said cylindrical portion further comprises at least one optical lens, said optical lens configured and sized to refract light being reflected by said conical mirror by a predetermined amount.

12. The surgical tool of claim 11, wherein said optical lens refracts light by said predetermined amount in a manner that reduces the magnification of the aortic structures being reflected and visible on said top portion, and whereby, in use, the measurement increments in said reflected array are closer together than the measurement increments in the actual array, and the aortic structures in contact with said external cylindrical surface appear on said top portion smaller than they actually are at the contact location with said surgical tool.

13. The surgical tool of claim 11, wherein said optical lens refracts light by said predetermined amount in a manner that increases the magnification of the aortic structures being reflected and visible on said top portion, and whereby, in use, the measurement increments in said reflected array are spaced further apart than the measurement increments in the actual array, and the aortic structures in contact with said external cylindrical surface appear on said top portion larger than they actually are at the contact location with said surgical tool.

14. A surgical tool for visually assessing the aortic structures contained within a generally tubular aortic root of a patient, the aortic root including an aortic valve, the aortic valve defining a valve axis, the aortic root extending in height along the valve axis between a root base portion located in proximity to a left ventricular outflow tract and a spaced away root sinotubular portion located in proximity to a sinotubular junction, the aortic valve attached to the aortic root through a scalloped valve annulus extending circumferentially around the valve axis, the aortic valve including a plurality of valve cusps connected to the valve annulus, the valve cusps each having a free margin portion spaced from the valve annulus, the free margin including a nodulus of arantius at a substantially midspan location, the valve cusps each defining a nadir at the attachment point with the valve annulus closest to the root base portion, the valve cusps having a geometric height defined by the distance between the nadir and nodulus of arantius, the valve cusps collectively defining commissures at the junction of each of two adjacent cusps in proximity to the valve annulus, said surgical tool comprising:

a substantially cylindrical portion, said cylindrical portion defining an external substantially cylindrical surface, said cylindrical portion extending in height along a tool axis between a base portion and a top portion, said cylindrical portion appropriately configured and sized for insertion within the aortic root, said cylindrical portion having a sufficiently optically clear section, whereby, in use, when said surgical tool is placed within the aortic root and the aortic structures are in contact with said external cylindrical surface, the aortic structures are visible through said optically clear section;

wherein said cylindrical portion is provided with a plurality of angularly spaced demarcation features, said demarcations being spaced a predetermined amount to allow marking of a tubular vascular prosthesis at said demarcation features when said prosthesis is placed over said cylindrical portion of surgical tool;

wherein said cylindrical portion is substantially hollow and defines a cavity therewithin, said cavity delimited in part by an internal substantially cylindrical surface, said internal cylindrical surface being offset inwardly from said external cylindrical surface to define an annular wall between said external and internal surfaces, said optically clear section contained within at least a portion of said annular wall, the aortic structures being visible when line of sight accesses said internal cylindrical surface; and wherein said surgical tool further comprises a generally elongate handle portion, said handle portion connected to said cylindrical portion for manipulating said surgical tool during insertion of said tool in the aortic root.

15. The surgical tool of claim 14, wherein said demarcation features consist of slots in said top portion of said cylindrical portion, said slots configured and sized to allow cutting of said tubular vascular prosthesis along said slot when the latter is placed over said cylindrical portion of surgical tool.

\* \* \* \* \*